US007323341B1

(12) United States Patent
Jasper

(10) Patent No.: US 7,323,341 B1
(45) Date of Patent: Jan. 29, 2008

(54) STABLE ISOTOPIC IDENTIFICATION AND METHOD FOR IDENTIFYING PRODUCTS BY ISOTOPIC CONCENTRATION

(76) Inventor: John P. Jasper, 8 Old Oak La., Niantic, CT (US) 06357

( * ) Notice: Subject to any disclaimer, the term of this patent is extended or adjusted under 35 U.S.C. 154(b) by 0 days.

(21) Appl. No.: 09/349,380

(22) Filed: Jul. 9, 1999

(51) Int. Cl.
*G01N 33/00* (2006.01)

(52) U.S. Cl. .......................... 436/56; 436/27; 436/173; 250/303; 250/260

(58) Field of Classification Search .................. 436/56, 436/27, 173; 250/303, 260; 702/22
See application file for complete search history.

(56) References Cited

U.S. PATENT DOCUMENTS

| | | | | |
|---|---|---|---|---|
| 5,012,052 | A | 4/1991 | Hayes | |
| 5,314,827 | A | 5/1994 | Schmidt et al. | |
| 5,424,539 | A * | 6/1995 | Brand et al. | 250/288 |
| 5,432,058 | A | 7/1995 | Lange, III et al. | |
| 5,474,937 | A | 12/1995 | Anderson, II et al. | |
| 5,677,187 | A | 10/1997 | Anderson, II et al. | |
| 5,760,394 | A | 6/1998 | Welle | |
| 5,830,763 | A | 11/1998 | Junk et al. | |
| 5,846,514 | A | 12/1998 | Foster et al. | |
| 6,057,542 | A | 5/2000 | Meijer et al. | |

OTHER PUBLICATIONS

Jamin, E., Naulet, N., and Martin, G.J., Multi-element and multi-site Isotopic analysis of nicotine from tobacco leaves; Plant, Cell and Environment (1997) 20, pp. 589-599.

Bommer, P., Moser, H., Stichler, W., Trimborn, P., Vetter, W. Herkunftsbestimmung von Arzneimitteln durch Messung von naturlichen Isotopenvarhaltnissen: D/H und 13C/12C Verhaltnisse elniger Proben von Diazepam. Z. Naturforsch 31, pp. 111-114, 1976.

* cited by examiner

*Primary Examiner*—Jill Warden
*Assistant Examiner*—Samuel P Siefke
(74) *Attorney, Agent, or Firm*—Krieg DeVault LLP

(57) ABSTRACT

A stable isotopic identification comprising a mathematical array of concentrations of isotopes found in a product, said mathematical array being presented in a machine readable form and comparable to analytical results whereby the product can be distinguished from other similar products, said machine readable form also being indexed through stored product information. The stored product information may be displayed when desired. By the stable isotopic identification of the invention, a product may be securely traced through manufacturing of a product, marketing of a product and the use of a product.

A method of identifying products is also provided utilizing the stable isotopic identification including the steps of analyzing a product for the concentration of isotopes, arranging the concentrations of the isotopes in a mathematical array, formulating the mathematical in a machine readable form, assembling product information, and indexing the product information to the machine readable form of the mathematical array, maintaining both the indexing and the product information, and when desired measuring the isotopic concentration of a comparable substance, comparing mathematical arrays, and accessing stored product information through the indexing of the same to product information, whereby a product may be traced through manufacturing, the marketplace and use, identified, and indexed to product information.

32 Claims, No Drawings

STABLE ISOTOPIC IDENTIFICATION AND METHOD FOR IDENTIFYING PRODUCTS BY ISOTOPIC CONCENTRATION

THE BACKGROUND OF THE INVENTION

The present invention relates to a stable isotopic identification and method for identifying products using naturally occurring isotopic concentrations or isotopic ratios in products, especially in the pharmaceutical industry, and more particularly to an identification and a method utilizing such isotopic concentrations or ratios in a machine readable form for identifying products and tracking products through manufacturing, marketing and use of a product, and readily indexing product information to the product.

The stable isotopic composition of matter has been recognized since about 1945 as a criterion for differentiating one material from another with the same elemental composition. In the field of geochemical oil exploration and prospecting, measurement of the isotopic compositions of large numbers of individual organic compounds of oil samples from various oil reservoirs have assisted in clarifying the origin of specific compounds correlating the organic compounds with particular petroleum sources, recognizing the existence of multiple petroleum sources, examining the mechanisms of petroleum generation, and improving the sensitivity of petroleum migration studies. This information, particularly in connection with seismological data, can be used to predict locations of other oil reservoirs to which oil may have migrated from a common source of generation or formation.

Isotope ratio monitoring has further applications in the biomedical field, wherein non-radioactive and stable isotopes are used as tracer labels in drug metabolism and other biomedical studies where natural variations in isotopic abundances may also carry additional information regarding sources and fates of metabolites. Current radioactive and stable isotopic labeling apparatus and methods in the medical fields employ typically costly labeled compounds having isotope ratios much different than those found in natural abundance. Since the inception of these techniques, improvements in isotope ratio monitoring sensitivity and precision, and a reduction in sample size and the required amount of the taggant material have occurred. In some cases, the relative concentration of the minor isotope versus the major isotope of naturally occurring isotopic ratios is so small that monitoring the isotope ratio has been problematic. It is therefore highly desirable to provide a new and improved stable isotopic identification and a method of identifying products utilizing a stable isotopic identification. It is also highly desirable to provide a new and improved stable isotopic identification and a method for identifying products utilizing the same which is fully operational utilizing naturally occurring variations in isotopic abundance, thus eliminating costly taggants in some applications.

In the combustible fuel, environmental, foods, explosive and ammunition and paint industries, the new and improved stable isotope identification can be used.

In the pharmaceutical industry, there is a need to trace ingredients through the manufacturing process, through the marketplace, and into various usages. Products such as active pharmaceutical ingredients (APIs), excipients of drug products, impurities in drug products, raw materials and drug products are included in those products which a pharmaceutical manufacturer may wish to trace. The ready identification of products in the marketplace allows a pharmaceutical manufacturer to monitor its products for quality purposes as well as to act as an impediment against fraudulent “knock-offs” or counterfeits. It is therefore highly desirable to provide a new and improved stable isotopic identification which can be used in the pharmaceutical industry for APIs, drug products, excipients of drug products, and/or impurities of drug products and a new and improved method of identifying and using such an identification. It is also highly desirable to provide a new and improved stable isotopic identification utilizing the intrinsic or ambient variability of the stable isotopic compositions or ratios of the product (not artificially altered or “tagged”) thereby eliminating the need for relatively expensive taggants and the resultant dilution or contamination by impurities of the product, and a method utilizing such isotopic concentrations or ratios in a machine readable form for identifying products, and tracking products through manufacturing, marketing and use of a product, and readily indexing product information to the product.

New techniques for measuring highly precise on-line isotopic ratios are now available. The probability of isotopic compositions of two batches from independent sources being the same is inversely proportional to the product of the dynamic ranges of each type of isotopic analysis undertaken, whether bulk or compound specific analyses. The “dynamic range” is defined herein as the range of values expected for a given type of measurement divided by the 1-sigma standard deviation of that measurement. All products such as APIs, drug products, excipients of drug products and/or impurities of drug products have intrinsic or ambient measurable amounts of stable isotopes of common light elements such as carbon, hydrogen, oxygen, nitrogen, sulfur, and chlorine. It is therefore highly desirable to provide a new and improved stable isotopic identification derived from stable isotopic compositions or ratios of common light elements of the product and a method of identifying the products and indexing product information to the product utilizing the same. It is also highly desirable to provide a new and improved stable isotopic identification for APIs, drug products, excipients of drug products and/or impurities of drug products which can be readily determined by either on-line or off-line analysis of the intrinsic, ambient or naturally occurring stable isotopic compositions or ratios of the common light elements in such products and a method for identifying and tracing such products throughout the manufacturing process, the marketplace and use and potential misuse.

Finally, it is highly desirable to provide a new and improved stable isotopic identification and method for utilizing the same including all of the above features throughout the chemical, petroleum, pharmaceutical, biomedical, food, environmental, paint, explosive-ammunition, and combustible fuel industries.

SUMMARY OF THE INVENTION

It is therefore an object of the invention to provide a new and improved stable isotopic identification, and a method of identifying products utilizing stable isotopic identification.

It is also an object of the invention to provide a new and improved stable isotopic identification, and a method for identifying products utilizing the same which is fully operational utilizing naturally occurring variations in isotopic abundance, thus eliminating costly taggants.

It is also an object of the invention to provide a new and improved stable isotopic identification which can be used in the pharmaceutical industry for APIs, drug products, excipients of drug products, and/or impurities of drug products, and a new and improved method of identifying and using such products.

It is also an object of the invention to provide a new and improved stable isotopic identification utilizing the intrinsic or ambient variability and the stable isotopic composition or ratios of the product (not artificially altered or "tagged") thereby eliminating the need for relatively expensive taggants and the resultant dilution or impurity of the product, and a method utilizing such isotopic concentrations or ratios in a machine readable form for identifying products and tracking products through manufacturing, marketing and use of a product, and readily indexing product information to the product.

It is also an object of the invention to provide a new and improved stable isotopic identification derived from stable isotopic compositions or ratios of the common light elements in products, and a method of identifying products and indexing product information to the product utilizing the same.

It is also an object of the invention to provide a new and improved stable isotopic identification for APIs, drug products, excipients of drug products and/or impurities of drug products which can be readily determined by either on-line or off-line analysis of the intrinsic, ambient or naturally occurring stable isotopic compositions or ratios of common light elements in such products and a method for identifying and tracing such products throughout the manufacturing process, the marketplace and use.

It is finally an object of the invention to provide a new and improved stable isotopic identification and method for utilizing the same including all of the above features throughout the chemical, petroleum, pharmaceutical, biomedical, food, environmental, paint, explosive-ammunition and combustible fuel industries.

In the broader aspects of the invention there is provided a stable isotopic identification comprising a mathematical or numerical array of concentrations of isotopes found in a product, said mathematical or numerical array being presented in a machine readable form and comparable to analytical results whereby the product can be distinguished from other similar products, said machine readable form also being indexed through stored product information. The stored product information may be displayed when desired. By the stable isotopic identification of the invention, a product may be securely traced through manufacturing of a product, marketing of a product and the use of a product.

A method of identifying products is also provided utilizing the stable isotopic identification including the steps of analyzing a product for the concentration of isotopes, arranging the concentrations of the isotopes in a mathematical or numerical array, formulating the mathematical or numerical array in a machine readable form, assembling product information, and indexing the product information to the machine readable form of the mathematical or numerical array, maintaining both the indexing and the product information, and when desired measuring the isotopic concentration of a comparable substance, comparing the mathematical or numerical arrays, and accessing stored product information through the indexing of the same to product information, whereby a product may be traced through manufacturing, the marketplace and use, identified, and indexed to product information.

DESCRIPTION OF A SPECIFIC EMBODIMENT

The present invention provides a stable isotopic identification of products and a method for utilizing such isotopic concentrations (which in a specific embodiment may be expressed in isotopic ratios) in a machine readable form for identifying products and tracking products through manufacturing, marketing and use of a product, and readily indexing product information to the product, especially with pharmaceutical phases, such as active pharmaceutical ingredients (APIs), drug products, the excipients of drug products and/or impurities of drug products utilizing concentrations of naturally occurring stable isotopes, and formulating a stable isotopic identifications therefrom. The present invention also provides a unique method for utilizing the stable isotopic identification of the invention and identifying products later in the manufacturing or the marketing or the use or misuse of the product and referencing the same to detail product information, serial numbers, or the like for identifying fraudulent products or "knock-offs" throughout the chemical, petroleum, pharmaceutical, biomedical, foodstuff, environmental paint, explosive-ammunition and combustible fuel industries.

The term "error" is used herein generically to refer to the deviation between a measured value and the true value of the measurement no matter how expressed. The term "precision" is used herein with regard to any group of multiple measurements to refer to the 1-sigma standard deviation of those measurements divided by the square root of the number of observations in the group of measurements.

Stable isotopes can be routinely measured by combustion and mass spectrometric analysis of either bulk phases or of specific compounds, by spectroscopic means. Bulk phases are analyzed by either off-line combustion followed by dual-inlet isotope ratio mass spectrometry (irMS) or by on-line combustion coupled with high resolution isotope ratio monitoring/mass spectrometry (irmMS). Specific compounds are analyzed by either gas chromatography coupled with irmMS (irmGCMS including CRIMS (Chemical Reaction Interface MS)) as disclosed in U.S. Pat. No. 5,012,052 issued to John M. Hayes on Apr. 30, 1991 or by liquid chromatography coupled with irmMS (irmLCMS), depending upon the chromatographic properties of the analytes. IrmGCMS including CRIMS allows for a continuous uninterrupted automated analysis whereas off-line methods require the samples to be purified into separate components and collected in batches (e.g., glass ampoules) prior to analysis. The concentrations monitored are generally recorded as isotopic ratios which are expressed as the concentration of the heavy isotope A divided by the concentration of lighter isotope B, e.g., $^{13}C/^{12}C$, D/H, $^{15}N/^{14}N$, $^{18}O/^{16}O$, $^{35}S/^{32}S$, etc. Each of these ratios will include the error of the concentration.

Ratios of isotopic concentrations are preferred as they present two distinct advantages over individual concentrations. First, isotopic ratios can be more reproducibly measured than compositions. Second, isotopic ratios may not be modified by non-nuclear physical or chemical processes or explosions such that ratios will remain intact through subsequent chemical reactions, including fires and explosions.

Further, isotopic concentrations provide stable isotopic identifications which are highly specific. Elements which have more than one stable isotope are numerous. Of the 83 known non-radioactive elements known to exist on earth, 62 have more than one stable isotope, and 40 have more than two stable isotopes. The element tin (Sn) has the largest number of stable isotopes for any single element. Among the 40 elements having more than two stable isotopes, there are a total of 224 stable isotopes. Although a few of the 224 stable isotopes are slightly radioactive, they have very long lives and are present in many naturally occurring elements. Thus, as will be seen, the stable isotopic identifications of the invention are numerous and provide a ready and available means by which any product (including all pharmaceutical phases APIs, drug products, excipients of drug products and/or impurities of drug products) may be readily identified.

If only the common light elements of carbon, hydrogen, oxygen, nitrogen and sulfur were used, there are 13 different stable isotopes. These 13 stable isotopes will provide ample means for providing a highly specific stable isotopic identification for any product desirably traced or desirably identified as will be explained as a specific embodiment hereinafter.

The Stable Isotopic Identification

The new and improved stable isotopic identification of the invention provides a highly specific, readable numerical array which can be used to identify each product desirably identified. The stable isotopic identification of different products or phases (such as APIs, drug products, excipients of drug products and/or impurities of drug products) or other isotopic compositions of a given phase or isotopic compositions of a combination of different phases provide a means by which any batched product and each of its precursors or raw materials or intermediates in a manufacturing process can be identified and traced through the manufacturing process, marketing of the product and the use and misuse of the product. The compositions used are usually stable isotope ratios measured by combustion and mass spectrometry analysis of either bulk phases or specific compounds.

The chemical analysis required to determine the stable isotopic ratios are classified as bulk stable isotopic composition (BSIA) or compound-specific isotopic composition (CSIA). These analyses are performed by high resolution irmMS or by nuclear magnetic resonance (NMR). Bulk phases are typically analyzed by either off-line combustion followed by dual inlet mass spectrometry or by on-line combustion coupled with irmMS. Specific compounds are analyzed by either irmGCMS including CRIMS or irmLCMS, depending upon the chromatographic properties of the analytes. NMR can be applied to either homogeneous bulk phases or to purified specific compounds.

Of course stable isotopic concentrations, not ratios, can also be measured by combustion and mass spectrometric analysis of either bulk phases or specific compounds by the same techniques in other specific embodiments. These concentrations instead of being expressed in ratios, i.e., $^{13}C/^{12}C$, D/H, $^{15}N/^{14}N$, $^{18}O/^{16}O$, $^{34}S/^{32}S$ etc., could merely be expressed in concentrations, e.g., 12 parts per million or 0.001 percent or parts per thousand or 0.001 weight percent, 0.001 mole percent, etc. or expressed with the measurement error, e.g., two parts per thousand plus or minus two parts per million or 0.001 mole percent plus or minus 0.0001 percent. Similarly, isotopic ratios can be presented in the same fashion as concentrations.

The new and improved stable isotopic identification of the invention is formulated from the concentrations or isotopic ratios of a selected group of one or more naturally occurring isotopes found in the product to be identified. Prior to formulating the isotopic identification of each product, one needs to determine what error in identifying the product is tolerable. The stable isotopic identification of the invention may include a simple list of a plurality of concentrations, a simple list of a plurality of isotopic ratios, a simple list of a plurality of mathematical products of isotopic concentrations, a simple list of a plurality of mathematical products of isotopic ratios, groups of any such lists, groups of any such mathematical products, groups of any such ratios, groups of any such concentrations, mathematical products of any such concentrations plus or minus their error added, mathematical products of any such ratios plus or minus their errors added, any of such concentrations, ratios, lists, groups and mathematical products in quadrature, isotopic ratios of any of such mathematical products, ratios of said concentrations plus or minus their errors added, any of said concentrations plus or minus their errors added, factor analysis of any such concentrations, ratios, lists, groups, and mathematical products and determinants and combinations thereof.

Thus, for example, if the tolerable error in identification of the product is the same or greater than the error in the concentration (stable isotope ratio), then simply a listing of the concentration of a stable isotope may serve as the stable isotopic identification of the invention. However, if in identification less error (or greater specificity) is desired, the probability of the two isotopic compositions of two separate batches from independent sources being the same is inversely proportional to the product of the dynamic ranges of each isotopic analysis undertaken; and thus, the acceptable or tolerable error of identification desired can be chosen by choosing any one of the above identified mathematical or numerical arrays involving more than one isotopic concentration.

Additionally, the "error of identification" can be reduced or, the "precision of identification" can be increased by choosing more than one isotopic concentration. There are a total of 13 if one limits the stable isotopic identification of the invention to the common light elements. Reduced error can be accomplished by using any number of the total of 252 available stable isotopes of elements having two or more stable isotopes.

Further, inasmuch as the specificity is inversely proportional to the product of the concentrations (statistically, the product of the dynamic ranges of each analysis), by use of a mathematical or numerical array including one or more of the above-identified mathematical products, the error of identification can even be further reduced or, "the specificity of identification can even be further increased". Still further, smaller errors of identification can be obtained by using concentrations and their error in quadrature, or in factor analysis, or in combinations thereof.

By the new and improved stable isotopic identification of the invention, the error of identification can be significantly reduced beyond most recognizable error (smaller than one part per million possibilities of incidental reproduction) such that identifications can be nearly guaranteed with use of the stable isotopic identification of the invention, and certainly within the error of the more publicized DNA identifications of from organic tissue.

Even with the limitation to common light elements (e.g., carbon, hydrogen, nitrogen and sulfur), identification of most products, pharmaceutical products, drug products, excipients and impurities can be identified with very little error (high precision), for example, by using a sample matrix of five isotopic ratios as shown in Table 1.

TABLE 1

| Istopic Ratio | Drug Product | API | Excipient #1 | Impurity #1 |
|---|---|---|---|---|
| Delta $^{13}C$ | $C_{dp}$ | $C_{api}$ | $C_{e1}$ | $C_{i1}$ |
| Delta D | $D_{dp}$ | $D_{api}$ | $D_{e1}$ | $D_{i1}$ |
| Delta $^{18}O$ | $O_{dp}$ | $O_{api}$ | $O_{e1}$ | $O_{i1}$ |
| Delta $^{15}N$ | $N_{dp}$ | $N_{api}$ | $N_{e1}$ | $N_{i}$ |
| Delta $^{34}S$ | $S_{dp}$ | $S_{api}$ | $S_{e1}$ | $S_{i1}$ |

The error is reduced, by compounding the precision of five analytical measurements. Table 1 records the isotopic ratios of five common light elements occurring in the four phases of a given pharmaceutical product. In fact, there may be more or fewer than 20 isotopic values indicated in any specific example. For example, the elements N and S may not occur in a given API or there may be more than one excipient or impurity. In all events, error in identification is very small and quantitatively constrained.

In the other specific examples including the mathematical or numerical arrays listed above, a variety of lists of concentrations, lists of concentration ratios, lists of mathematical products of concentrations or groups of lists or concentrations, or ratios or mathematical products or mathematical products of concentrations and errors may be placed in a matrix such as shown in Table 1 to provide a stable isotopic identification of the invention for any product known with a degree of specificity that can be predicted (the probability that the isotopic compositions of two batches or phases from independent production sources are the same) that is inversely proportional to the product of the dynamic ranges for each isotopic analysis undertaken whether they are bulk or compound specific analyses.

The "dynamic range" is defined herein as the range of values expected for a given type of measurement divided by the 1-sigma standard deviation of that measurement.

For example, for one bulk isotopic measurement performed on a subsample of a number of homogenized drug products from a given batch, the random probability of another manufacturer producing the same bulk isotopic value is estimated at about one in one hundred, or 0.01. In fact, the probability may be less than that depending upon the isotopic ranges of the production phases. A simple calculation is based upon a conservative one-sigma value for the standard deviation in the bulk isotopic measurement of 0.1‰, with a 10‰ range in the isotopic range in the bulk materials (viz., the Dynamic Range=10‰/0.1‰=100, the probability=0.01).

In the second example, where two or more isotopic compositions are measured, for example, one bulk analysis and one compound-specific analysis, the random probabilities of another manufacturer producing two similar isotopic values decreases multiplicatively by orders of magnitude, for example, 0.01×0.01=0.0001, or 1 in 10,000. Recalling that both types of compound-specific analyses typically generate a number of isotopic analyses of whatever is chromatographable in the sample (often approximately 100 individual compounds), whether an API or excipient or a drug product or an impurity or another product, the probability of another manufacturer producing a product with a similar isotopic composition is vanishingly small. Thus, such a stable isotopic identification of the invention for any given batch may be virtually unique or highly specific (significantly smaller than 1 part per million).

For purposes of comparison, results of BSIA and/or CSIA analyses can be expressed in three ways: a simple column, a table like Table 1, or in mathematical determinants. The salient point is to uniquely connect stable isotopic identifications of a product to measured isotopic values for later retrieval and comparison to sample or suspect pharmaceutical phases. In accordance with the invention, these may be indexed in the form of serial numbers or a machine readable bar code display on a container for the product or both.

In specific embodiments, the mathematical or numerical array of the stable isotopic identification of the invention may be in tabular or matrix form as above described. When using a tabular or matrix or mathematical or numerical array, computerized sorting of the tabular rows and columns of isotopic values by increasing or decreasing values of individual isotopic concentrations will reveal whether or not a sample or suspect isotopic value would fit into the table or matrix as an initial test of specificity. Overlap of the sample isotopic value (e.g., within error limits) indicates a possible match with a pre-existing possible match with the stable isotopic identification of the invention which can be addressed through standard statistical techniques of comparison. Further comparison of the isotopic values of the stable isotopic identification allows a stepwise comparison of the other isotopic values of the stable isotopic identification. The lack of a match with any previously tabulated isotopic value indicates a different and distinguishable product or pharmaceutical phase perhaps a counterfeit product.

By contrast, a match with a previously identified isotopic value indicates one of three possibilities: (1) a new and unique isotopically defined pharmaceutical phase isotopic value that exists within the statistical limits defined by the ranges of the isotopic value considered, (2) the highly unlikely possibility of a coincidental match (within limits defined by the isotopic range of the product considered), or (3) the extremely unlikely possibility of a fraudulent synthesized isotopic match. If the isotopic value does not overlap with any previous stable isotopic identification, then it shall be considered a new and different and distinguishable composition. If it does not match a firm's list of stable isotopic identifications for that firm's batches or products, then the observed stable isotopic identification indicates a product not produced by the firm.

In other specific embodiments, combination by multiplication of isotopic values within a stable isotopic identification of the invention (plus or minus the error of the measurements added in quadrature) will result in a highly specific stable isotopic identification which can be used as a batch's serial number or added to a serial number. For example, the identification may be stated as:

$$(\square^{13}C*\square^{15}N)*[1+/-([1\square-\square^{13}C/\square\square^{13}C]^2+[1\square-\square^{15}N/\square\square^{15}N]^2)^{0.5}]$$

As with the tabular method above, the lack of matching with previously recorded values indicates a distinctly different product. But this method requires only that the investigator sort the isotopic data by one column (as opposed to sorting by each isotopic value). This method also hides the individual isotopic values of the sample from all but those who have the original isotopic values of each component.

Finally, factor analysis with specific intervals around data clusters may be used to delineate specific sets of isotopically defined products. Samples that have stable isotopic identifications which fall within the confidence intervals of data clusters shall be considered statistically from the same batch of products. Those falling without the confidence intervals shall be considered to be distinctly different products.

THE METHOD OF THE INVENTION

The method of identifying products of the invention utilizing stable isotopic identifications takes the advantage of the natural variability in the product of isotopic compositions based on the product and their raw materials. Two classes of analytes are analyzed for their isotopic composition include bulk properties (bulk solids, liquids, or gases) and molecular properties (i.e., in pharmaceuticals, specific compounds such as APIs, excipients, and impurities).

These analytes are typically analyzed by one of two methods: Bulk properties are either measured in a stepwise combustion-analysis mode by either dual inlet mass spectrometry (off-line) or in a continuous combustion-analysis mode by irMS (on-line). In the off-line method, bulk analytes are typically prepared by combustion for analysis in sealed ampoules from which carbon dioxide ($CO_2$) or other combustion gases are cryogenically distilled. In the on-line method (also known as BSIA), an automated, on-line combustion device (e.g., an elemental analyzer) combusts bulk organic matter into gases (for example, $CO_2$, $N_2$,). Those gases may either be directly or indirectly isotopically analyzed, depending on the necessity for chemical reduction. The combustion and reduction steps are followed by isothermal packed-column chromatography that resolves the gaseous products prior to isotopic analysis. The stable isotopic analysis of specific compounds (CSIA) is typically performed either by irmGCMS including CRIMS or irmLCMS. The selection of the method depends on the chromatographic characteristics of the analyte. In the CSIA methods, organic analytes are separated by either gas chromatography or by liquid chromatography. The organic effluent is then combusted in an on-line combustion oven, and the effluent gases (typically, $CO_2$ or $N_2$) are isotopically analyzed by an on-line high-resolution mass spectrometer. Carbon isotopic results are typically expressed in either atom percent of the less abundant isotope or delta values (parts per thousand differences from a standard defined as:

$$\square^{13}C(‰)=[(R_{sample}/R_{standard})-1]*(1000)$$

where: $R_{smpl}$=the $^{13}C/^{12}C$ ratio of the sample material and the $R_{std}$ is the $^{13}C/^{12}C$ ratio of an International Atomic Energy Authority standard (known as "VPDB" whose $^{13}C/^{12}C$ ratio has been defined as the official zero point of the carbon-isotopic scale). Other stable isotope ratios are similarly expressed.

In another specific embodiment, isotopic analyses of either bulk drug products, APIs, excipients, or impurities can also be performed using NMR spectroscopy.

In another specific embodiment, the use of bulk stable isotopic analysis (BSIA) for drug products, for example, pills, salves, evaporated liquids, etc., via either off-line (ampoulated) or on-line high resolution mass spectrometry or the use of NMR spectroscopy can also be achieved.

In another specific embodiment, the use of compound-specific analysis (CSIA) for the analysis of Active Pharmaceutical Ingredients (APIs) via either irmGCMS including CRIMS, irmLCMS, or by NMR spectroscopy, depending on the nature of the analyte can also be achieved.

In another specific embodiment, the use of CSIA for the analysis of excipients in drug products via either irmGCMS including CRIMS, irmLCMS or by NMR spectroscopy, depending on the nature of the analyte can also be achieved.

In another specific embodiment, the use of CSIA for the analysis of impurities in drug products via either irmGCMS including CRIMS, irmLCMS or by NMR spectroscopy, depending on the nature of the analyte can also be achieved.

The same analytical procedures can be used to identify other products, such as organic products, such as gunpowder and other explosives, crude oil, foodstuffs, petroleum distillates, hazardous waste, paper and/or ink, and tire materials.

Once the product is analyzed with the concentration of isotopes and the concentration of each of the stable isotopes of the total of 252 stable isotopes available, which will form a part of the stable isotopic identification of the invention have been analyzed, the concentrations are arranged in a mathematical or numerical array and the array is formulated into a readable form and placed on the product or its container. This mathematical or numerical array could be part of the serial number, or it could be separately identified, or it could be a bar code on the product. The mathematical or numerical array may be in the form as above described, and in a specific embodiment, may be chosen from the group of mathematical or numerical arrays consisting of a list of a plurality of concentrations, a list of a plurality of isotope ratios, a list of a plurality of products, or a list of a plurality of products of concentrations and errors.

The array could also be a matrix as shown in Table 1 or connected to serial numbers or formulated in tabular form or ratio form or mathematical product form or in quadrature or in factor analysis or any combinations thereof. Each of these forms are described hereinabove with regard to the stable isotopic identification of the invention.

The mathematical or numerical array is then formulated into a readable form. This could be a set of numbers in a machine readable language or in a bar code or in such other machine readable form. The machine readable form could be part of a serial number or part of a product identification.

The product information, such as ingredient identifications, formulations, etc., is then assembled. With regard to pharmaceutical products, physician directed information could all be assembled as a part of the product information.

The product information is then indexed to the aforementioned readable form. A machine readable form could be read by a machine by which one would then view the product information on a screen, scroll through the product information and/or print out the sought for information, as required. Both the index and the product information would be maintained such that the product information could be accessed by machine from the machine readable form of the stable isotopic identification of the invention.

The method of the invention further comprises the steps of measuring the concentrations of the chosen isotopes of an unknown product in the same manner as the product identified by the stable isotopic identification of the invention was analyzed as above described, and comparing the stable isotopic identification of the known product with the isotopic analyses of the unknown product. This can be achieved in a number of ways. Whenever the stable isotopic identification is an array of more than concentration, ratio or product, the comparison may involve any of the statistically step by step comparisons of each ratio, concentration or product to an identification of product and the error desired. Once a product has been identified through its stable isotopic identification number, all of the product information that has been assembled can be found through the index.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A method for objectively identifying a known product, comprising:

obtaining isotopic data from elements present in said product;

providing a mathematical array that includes the isotopic data, the mathematical array being fixed in a readable form, said readable form with said mathematical array fixed thereon being an identification of said product;

wherein the isotopic data does not include data obtained from a taggant; and wherein the product consists essentially of a pharmaceutical product.

2. The method in accordance with claim 1 wherein the product does not include a taggant.

3. The method of claim 1 wherein said elements are selected from the group of elements consisting of carbon, hydrogen, oxygen, nitrogen, sulphur and combinations thereof, said isotopes being any of the thirteen stable isotopes thereof.

4. The method of claim 1, wherein said data is determined by an analysis selected from the group of analyses consisting of bulk phase analysis and specific compound analysis.

5. The method of claim 4, wherein said bulk phase analysis includes off-line dual Inlet Isotope ratio mass spectrometry (irMS) and on-line combustion coupled with high resolution isotope ratio monitoring/mass spectrometry (irmMS).

6. The method of claim 4, wherein said specific compound analysis includes gas chromatography coupled with irMS (irmGCMS) and liquid chromatography coupled with irMS (irmLCMS).

7. The method of claim 4, wherein said analysis includes nuclear magnetic resonance.

8. A method for objectively identifying a known product, comprising:

obtaining isotopic data from elements present in said product;

providing a mathematical array that includes the isotopic data, the mathematical array being fixed in a readable form, said readable form having said mathematical array fixed thereon being an identification of said product;

wherein the isotopic data comprises isotopic data for at least one isotope of an element selected from the group consisting of carbon, hydrogen, nitrogen, oxygen and sulfur; and wherein the product consists essentially of a pharmaceutical product.

9. The method of claim 8 wherein said isotopic data comprises data selected from the group consisting of one or more intrinsic concentrations of isotopes, one or more ratios of intrinsic concentrations of two isotopes, one or more mathematical products of intrinsic isotopic concentrations or ratios, one or more lists of a plurality of mathematical products of intrinsic isotopic concentrations or ratios, one or more groups of any such lists, one or more groups of any such mathematical products, one or more groups of any such ratios, one or more groups of any such concentrations, one or more mathematical products of any such concentrations plus or minus their error added, one or more mathematical products of any such ratios plus or minus their error added, any such concentrations, ratios, lists, groups and mathematical products in quadrature, one or more of any such concentrations plus or minus their errors added, one or more of any such ratios plus or minus their errors added, factor analysis of any such concentrations, ratios, lists, groups, mathematical products, and any determinants and combinations thereof present in said product.

10. The method of claim 8 wherein at least a portion of said mathematical array fixed in a readable form is associated with said product through manufacturing, marketing and use.

11. The method of claim 8 wherein said mathematical array and product information associated with the product are fixed in machine readable form.

12. The method of claim 11 wherein said mathematical array and said product information are indexed to said product in the form of machine readable serial numbers, bar codes, and other numerical and alphabetical indicia.

13. The method of claim 8 wherein said elements are selected from the group of elements consisting of carbon, hydrogen, oxygen, nitrogen, sulphur and combinations thereof, said isotopes being any of the thirteen stable isotopes thereof.

14. The method of claim 8 wherein said elements are selected from the group of elements that have more than two isotopes, said isotopes being any of the 224 stable isotopes thereof.

15. The method of claim 11, wherein said mathematical array is indexed to said product information in said readable form.

16. The method of claim 11, wherein said product information is in a form operable to be scrolled, downloaded or printed.

17. The method of claim 8, wherein said elements are selected from the group of elements that have two isotopes.

18. The method of claim 8, wherein said isotopes are selected from the group consisting of the 13 stable isotopes of a group of elements consisting of carbon, hydrogen, oxygen, nitrogen, sulphur and combinations thereof.

19. The method of claim 8, wherein an error of identification is selected based upon the mathematical array chosen, the number of concentrations of isotopes utilized in said array, and the portion of said first array compared with a second array.

20. The method of claim 8, wherein said concentrations of isotopes are determined by an analysis selected from the group of analyses consisting of bulk phase analysis and specific compound analysis.

21. The method of claim 20, wherein said bulk phase analysis includes off-line dual inlet isotope ratio mass spectrometry (irMS) and on-line combustion coupled with high resolution isotope ratio monitoring/mass spectrometry (irmMS).

22. The method of claim 20, wherein said specific compound analysis includes gas chromatography coupled with irMS (irmGCMS) and liquid chromatography coupled with irMS (irmLCMS).

23. The method of claim 20, wherein said analysis includes nuclear magnetic resonance.

24. The method of claim 11 wherein said mathematical array and said product information are stored in memory on a machine; wherein said machine readable forms and product information are indexed; and wherein said machine readable forms once identified through the index presents stored product information in displayed form.

25. The method of claim 24, wherein said product information may be scrolled through.

26. The method of claim 24, wherein said product information may be printed.

27. The method of claim 24, wherein said product information may be accessed through said index from said machine readable form of said mathematical array.

28. The method of claim 20 wherein said bulk phase analysis and said specific compound analysis each has a dynamic range equal to the observed range divided by the 1-sigma standard deviation.

29. The method of claim 20 wherein the precision of said bulk phase analysis and said specific compound analysis is the 1-sigma standard deviation of the analysis performed divided by the square root of the number of observations of said analysis.

30. The method of claim 8 wherein said obtaining step comprises obtaining intrinsic isotopic concentrations of $C^{13}$, $N^{15}$, $O^{18}$ and $H^3$ in a sample; and wherein the specificity of said determining is calculated by the following equation:

$$\text{Specificity}=(1\sigma-\delta^{13}C/\Delta\delta^{13}C)*(1\sigma-\delta^{15}N/\Delta\delta^{15}N)*(1\sigma-\delta^{18}O/\Delta\delta^{18}O)*(1\sigma-\delta D/\Delta\delta D).$$

31. The method of claim 8 wherein the specificity of said determining is inversely proportional to the product of the dynamic ranges of said isotopic analyses undertaken of said sample.

32. The method of claim 28 wherein the dynamic range is the range of values expected for an analysis divided by the 1-sigma standard deviation of that analysis.

* * * * *